(12) United States Patent
Okada et al.

(10) Patent No.: US 9,371,291 B2
(45) Date of Patent: Jun. 21, 2016

(54) PROCESS FOR THE MANUFACTURE OF THE CALCIUM SALT OF ROSUVASTATIN (E)-7-[4-(4-FLUOROPHENYL)-6-ISOPROPYL-2-[METHYL(METHYLSULFONYL)AMINO]-PYRIMIDIN-5-YL](3R,5S)-3,5-DIHYDROXYHEPT-6-ENOIC ACID AND CRYSTALLINE INTERMEDIATES THEREOF

(75) Inventors: Tetsuo Okada, Osaka (JP); John Horbury, Bristol (GB); David Dermot Patrick Laffan, Macclesfield (GB)

(73) Assignees: AstraZeneca UK Limited, London (GB); Shionogi & Company Limited, Osaka (JP)

( * ) Notice: Subject to any disclaimer, the term of this patent is extended or adjusted under 35 U.S.C. 154(b) by 270 days.

(21) Appl. No.: 13/186,363

(22) Filed: Jul. 19, 2011

(65) Prior Publication Data
US 2011/0301348 A1  Dec. 8, 2011

Related U.S. Application Data

(62) Division of application No. 10/576,774, filed as application No. PCT/GB2004/004481 on Oct. 22, 2004, now abandoned.

(51) Int. Cl.
*C07D 239/42* (2006.01)
*C07D 405/06* (2006.01)

(52) U.S. Cl.
CPC .......... *C07D 239/42* (2013.01); *C07D 405/06* (2013.01); *Y02P 20/55* (2015.11)

(58) Field of Classification Search
CPC ........................... C07D 239/42; C07D 405/06
USPC ........................................................ 544/332
See application file for complete search history.

(56) References Cited

U.S. PATENT DOCUMENTS

| | | | |
|---|---|---|---|
| 4,645,858 A | 2/1987 | Lowrie et al. | |
| 4,970,313 A | 11/1990 | Wess et al. | |
| 4,977,279 A | 12/1990 | Wess et al. | |
| 5,026,698 A | 6/1991 | Fujikawa et al. | |
| 5,278,313 A | 1/1994 | Thottathil et al. | |

(Continued)

FOREIGN PATENT DOCUMENTS

| | | |
|---|---|---|
| CA | 2545316 | 5/2005 |
| EP | 0319847 A2 | 6/1989 |

(Continued)

OTHER PUBLICATIONS

Hiyama et al. "Synthesis of Artificial HMG-CoA Reductase Inhibitors Based on the Olefination Strategy" Bull. Chem. Soc. Jpn. 68 (1):364-372 (1995).

(Continued)

Primary Examiner — Deepak Rao
(74) Attorney, Agent, or Firm — Morgan, Lewis & Bockius LLP

(57) ABSTRACT

A process for the manufacture of the calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid, useful as an HMGCoA reductase inhibitor, from a compound of the formula (7)

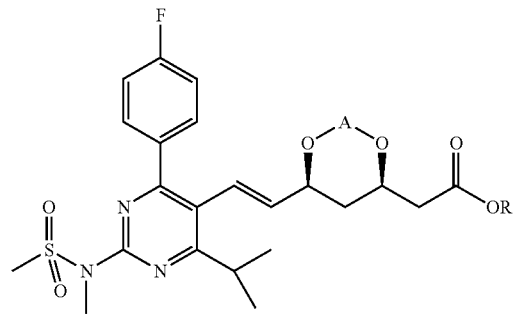

wherein A is an acetal or ketal protecting group and R is alkyl, via isolated crystalline compounds of the formula (8) or of formula (10)

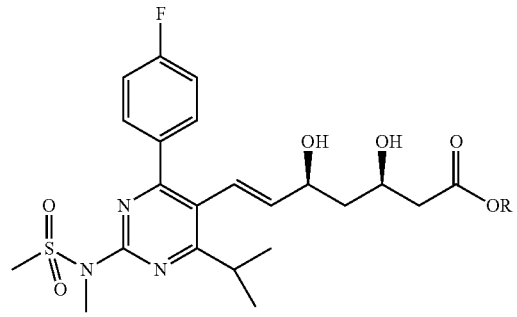

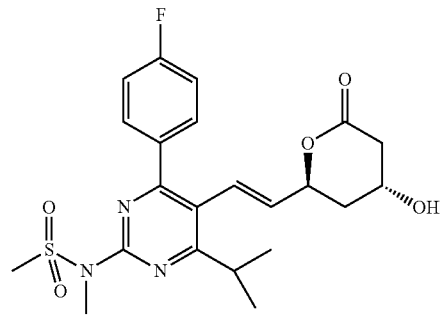

is described. Crystalline intermediates of formulae 7, 8 and 10 are also described.

4 Claims, 8 Drawing Sheets

(56) References Cited

U.S. PATENT DOCUMENTS

| | | | |
|---|---|---|---|
| 5,399,722 A | 3/1995 | Beck et al. |
| 5,594,153 A | 1/1997 | Thottathil et al. |
| 6,278,001 B1 | 8/2001 | Solladie et al. |
| 6,331,641 B1 | 12/2001 | Taoka et al. |
| 6,583,295 B1 | 6/2003 | Pflaum |
| 6,784,171 B2 | 8/2004 | Taylor et al. |
| 6,844,437 B1 | 1/2005 | Taylor et al. |
| 6,870,059 B2 | 3/2005 | Kooistra et al. |
| 6,875,867 B2 | 4/2005 | Brodfuehrer et al. |
| 7,157,255 B2 | 1/2007 | Blacker et al. |
| 7,304,156 B2 | 12/2007 | Matsushita et al. |
| 7,416,865 B2 | 8/2008 | Blacker et al. |
| 7,442,811 B2 | 10/2008 | Bakel Van et al. |
| 7,511,140 B2 | 3/2009 | Horbury et al. |
| 7,524,955 B2 | 4/2009 | Newton et al. |
| 7,642,363 B2 | 1/2010 | Kooistra et al. |
| 7,718,812 B2 | 5/2010 | Hof et al. |
| 7,732,171 B2 | 6/2010 | Blacker et al. |
| 7,816,528 B2 | 10/2010 | Matsushita et al. |
| 2003/0018199 A1 | 1/2003 | Brodfuehrer et al. |
| 2003/0114685 A1 | 6/2003 | Niddam-Hildesheim et al. |
| 2005/0090674 A1 | 4/2005 | Hof |
| 2005/0124639 A1 | 6/2005 | Joshi et al. |
| 2005/0209259 A1 | 9/2005 | Huang |
| 2006/0004200 A1 | 1/2006 | Gudipati et al. |
| 2006/0293355 A1 | 12/2006 | Booth et al. |
| 2007/0105882 A1 | 5/2007 | Black et al. |
| 2008/0058520 A1 | 3/2008 | Matsushita et al. |
| 2008/0188657 A1 | 8/2008 | Lenger |
| 2008/0207903 A1 | 8/2008 | Butters et al. |
| 2008/0221323 A1 | 9/2008 | Crabb et al. |
| 2008/0280336 A1 | 11/2008 | Blacker et al. |
| 2009/0264654 A1 | 10/2009 | Newton et al. |
| 2009/0286819 A1 | 11/2009 | Horbury et al. |
| 2010/0136339 A1 | 6/2010 | Kooistra et al. |
| 2010/0209984 A1 | 8/2010 | Blacker et al. |
| 2010/0222373 A1 | 9/2010 | Booth et al. |
| 2010/0228028 A1 | 9/2010 | Butters et al. |

FOREIGN PATENT DOCUMENTS

| | | |
|---|---|---|
| EP | 0521471 | 1/1993 |
| IN | 1304/DEL/2003 | 10/2003 |
| WO | WO 90/03973 | 4/1990 |
| WO | WO 93/08823 | 5/1993 |
| WO | WO 97/03959 | 2/1997 |
| WO | WO 97/19917 | 6/1997 |
| WO | WO 97/49681 | 12/1997 |
| WO | WO 00/42024 | 7/2000 |
| WO | WO 00/49014 | 8/2000 |
| WO | WO 01/22962 | 4/2001 |
| WO | WO 01/36384 | 5/2001 |
| WO | WO 01/54669 | 8/2001 |
| WO | WO 01/60804 | 8/2001 |
| WO | WO 01/72706 | 10/2001 |
| WO | WO 01/85702 | 11/2001 |
| WO | WO 01/85975 | 11/2001 |
| WO | WO 02/06266 | 1/2002 |
| WO | WO 02/30415 | 4/2002 |
| WO | WO 02/43667 | 6/2002 |
| WO | WO 02/43732 | 6/2002 |
| WO | WO 02/072566 | 9/2002 |
| WO | WO 02/083637 | 10/2002 |
| WO | WO 02/098854 | 12/2002 |
| WO | WO 03/006439 | 1/2003 |
| WO | WO 03/016317 | 2/2003 |
| WO | WO 03/018555 | 3/2003 |
| WO | WO 03/026573 | 4/2003 |
| WO | WO 03/059901 | 7/2003 |
| WO | 03/070717 A1 | 8/2003 |
| WO | WO 03/087112 | 10/2003 |
| WO | WO 03/097614 | 11/2003 |
| WO | WO 03/106447 | 12/2003 |
| WO | WO 2004/014872 | 2/2004 |
| WO | WO 2004/052867 | 6/2004 |
| WO | WO 2004/054986 | 7/2004 |
| WO | WO 2004/089895 | 10/2004 |
| WO | WO 2004/103977 | 12/2004 |
| WO | WO 2004/108691 | 12/2004 |
| WO | WO 2005/005384 | 1/2005 |
| WO | WO 2005/023778 | 3/2005 |
| WO | WO 2005/023779 | 3/2005 |
| WO | WO 2005/028450 | 3/2005 |
| WO | WO 2005/030215 | 4/2005 |
| WO | WO 2005/040134 | 5/2005 |
| WO | WO 2005/042522 | 5/2005 |
| WO | WO 2005/047276 | 5/2005 |
| WO | WO 2005/051921 | 6/2005 |
| WO | WO 2005/054207 | 6/2005 |
| WO | WO 2005/056534 | 6/2005 |
| WO | WO 2005/063728 | 7/2005 |
| WO | WO 2005/068435 | 7/2005 |
| WO | WO 2005/077916 | 8/2005 |
| WO | WO 2005/077917 | 8/2005 |
| WO | WO 2005/092867 | 10/2005 |
| WO | WO 2006/017357 | 2/2006 |
| WO | WO 2006/035277 | 4/2006 |
| WO | WO 2006/067456 | 6/2006 |
| WO | WO 2006/079611 | 8/2006 |
| WO | WO 2006/089401 | 8/2006 |
| WO | WO 2007/007119 | 1/2007 |

OTHER PUBLICATIONS

IP.com Prior Art Database, Technical Disclosure "Tert-butyl-7-[4-(4-fluorophenyl)-6-isopropyl-2-(N-methyl-N-methylsulfonylamino)pyrimidin-5-yl]-(3R,5S)-dihydroxy-(E)-6-heptenate crystal form" IP.com No. IPCOM000019023D (Aug. 27, 2003).

Kaneko et al. "Preparation of optically active 5,6-epoxyhexanoic acid esters as materials for physiologically active substances" Chemical Abstracts + Indexes, American Chemical Society, Columbus, US 118(11):832 (1993).

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Minami et al. "A Novel Enantioselective Synthesis of HMG Co-A Reductase Inhibitor NK-104 and a Related Compound" Tetrahedron letters 33(49):7525-7526 (1992).

Minami et al. "Stereoselective Reduction of β,-Diketo Esters Derived From Tartaric Acid. A Facile Route to Optically Active 6-oxo-3,5-syn-isopropylidenedioxyhexanoate, a Versatile Synthetic Intermediate of Artificial HMG Co-A Reductase Inhibitors" Tetrahedron Letters 34(3):513-516 (1993).

Moore et al. "Biosynthesis of the hypocholesterolemic agent mevinolin by *Aspergillus terreus*. Determination of the origin of carbon, hydrogen, and oxygen atoms by carbon-13 NMR and mass spectrometry" J. Am. Chem. Soc. 107(12): 3694-3701 (1985).

Nezasa et al. "Pharmacokinetics and disposition of rosuvastatin, a new 3-hydroxy-3-methylglutaryl coenzyme A reductase inhibitor, in rat" Xenobiotica 32(8):715-727 (2002).

Observations made by a third party concerning patentability of the invention in the corresponding EP Application No. 04768997.1, (Jan. 2010).

Prasad et al. "A novel diastereroselective synthesis of lactone moiety of compactin" Tetrahedron Letters 25(23):2435-2438 (1984).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Sakaki et al. "Lipase-catalyzed asymmetric synthesis of 6-(3-chloro-2-hydroxypropyl)-1,3-dioxin-4-ones and their conversion to chiral 5,6-epoxyhexanoates" Tetrahedron: Asymmetry 2(5):343-346 (1991).

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

(56) References Cited

OTHER PUBLICATIONS

Solladié et al. "Chrial Sulfoxides in Asymmetric Synthesis: Enantioselective Synthesis of the Lactonic Moiety of (+)-Compactin and (+)-Mevinolin. Application of a Compactin Analogue" J. Org. Chem. 60:7774-7777 (1995).
Watanabe et al. "Synthesis and Biological Activity of Methanesulfonamide Pyrimidine- and N-Methanesulfonyl Pyrrole-Substituted 3,5-Dihydroxy-6-heptenoates, a Novel Series of HMG-CoA Reductase Inhibitors" Bioorganic & Medicinal Chemistry 5(2):437-444 (1997).
Wess et al. "Stereoselective Synthesis of HR 780 A New Highly Potent HMG-CoA Reductase Inhibitor", Tetrahedron Letters 31(18): 2545-2548 (1990).
Examination Report issued in corresponding European Patent Application No. 04768997.1 dated Nov. 3, 2006.
Examination Report issued in corresponding European Patent Application No. 04768997.1 dated May 29, 2008.
Observations filed against patentability of European Patent Application No. 04768997.1 dated Jan. 8, 2009.
Examination Report issued in corresponding European Patent Application No. 04768997.1 dated Apr. 9, 2009.
Examination Report issued in corresponding European Patent Application No. 04768997.1 dated Feb. 8, 2011.
Examination Report issued in corresponding European Patent Application No. 04768997.1 dated Aug. 2, 2011.
Notice of Opposition and Statement of Grounds of Opposition filed in corresponding European Patent 1682536 dated Nov. 26, 2013.
Casey et al., "Advanced Practical Organic Chemistry," Blackie, 147-151 (1990).
Summons to attend oral proceedings issued in corresponding European Patent Application No. 04768997.1 dated Oct. 23, 2014.
Norris, "Experimental Organic Chemistry," Second Edition. McGraw Hill, 3-5 (1924).
Vogel, "A Text-Book of Practical Organic Chemistry," Longman, Third Edition, 122-136 (1956).
Response by Proprietors to Summons to attend Oral Proceedings issued in corresponding European Patent No. 1682536 dated Feb. 23, 2015 (including 1st to 12th Auxiliary Requests).
Submissions in response to Summons to attend Oral Proceedings issued in corresponding European Patent No. 1682536 dated Feb. 23, 2015.
Written Decision from Opposition Division of the European Patent Office issued in corresponding European Patent Application No. 04768997.1 dated May 18, 2015.
Grounds of Appeal submitted in corresponding European Patent Application No. 04768997.1 dated Sep. 18, 2015.
Tempkin et al., "Asymmetric Synthesis of 3,5-Dihydroxy-6(E)-heptenoate-containing HMG-CoA Reductase Inhibitors," Tetrahedron, 53: 10659-10670 (1997).
Expert declaration of Professor Laufer with CV submitted with Grounds of Appeal in corresponding European Patent Application No. 04768997.1 dated Sep. 14, 2015.

Figure 1: Methyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate
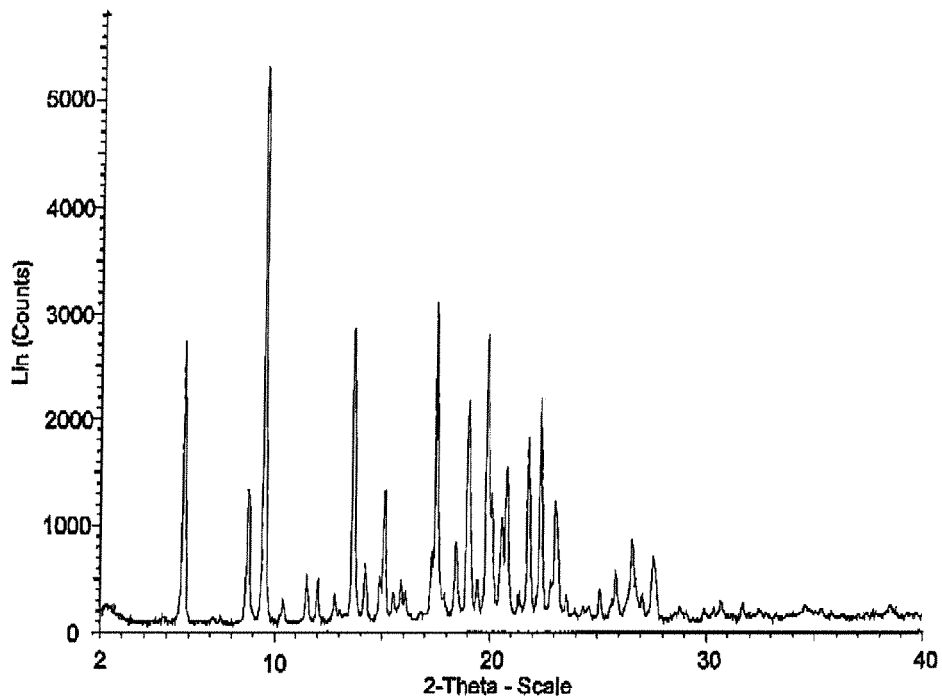
| 2-theta | d-spacing | Relative Intensities |
|---|---|---|
| 5.7 | 15.4 | 51 |
| 8.7 | 10.1 | 25 |
| 9.5 | 9.3 | 100 |
| 13.6 | 6.5 | 54 |
| 17.5 | 5.1 | 58 |
| 19.0 | 4.7 | 41 |
| 19.9 | 4.5 | 53 |
| 20.8 | 4.3 | 29 |
| 21.8 | 4.1 | 34 |
| 22.4 | 4.0 | 41 |

Figure 2: Ethyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate
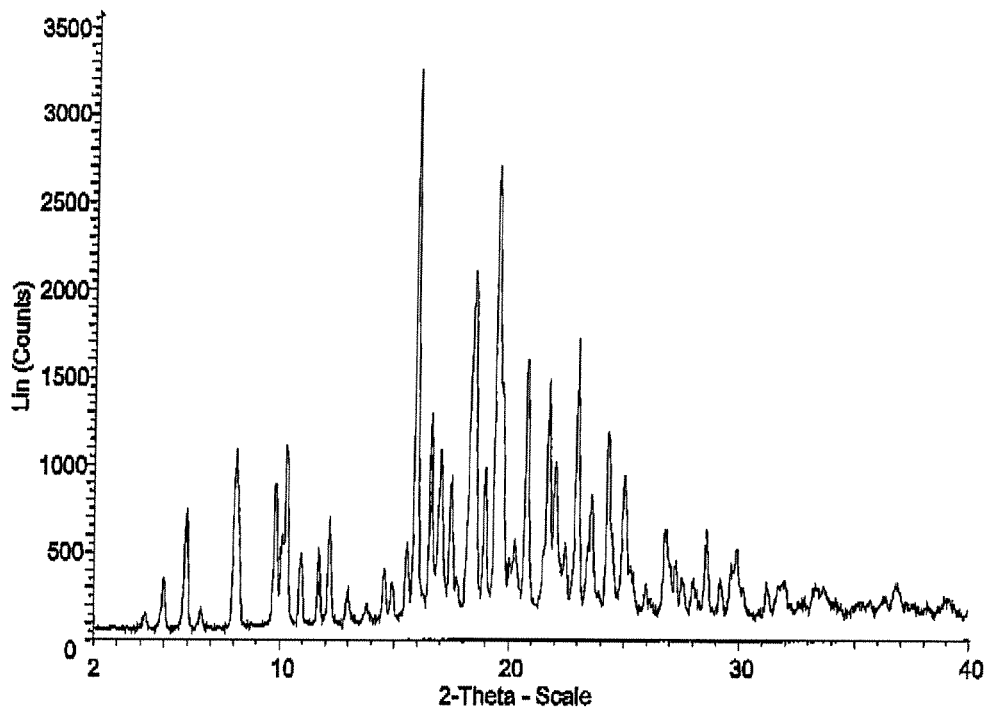
| 2-theta | d-spacing | Relative Intensities |
|---|---|---|
| 5.9 | 15.0 | 23 |
| 8.0 | 11.0 | 33 |
| 12.2 | 7.3 | 21 |
| 15.9 | 5.6 | 100 |
| 18.4 | 4.8 | 65 |
| 19.5 | 4.6 | 82 |
| 19.7 | 4.5 | 45 |
| 23.0 | 3.9 | 53 |
| 24.3 | 3.7 | 37 |
| 25.0 | 3.6 | 29 |

Figure 3: iso-Propyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate
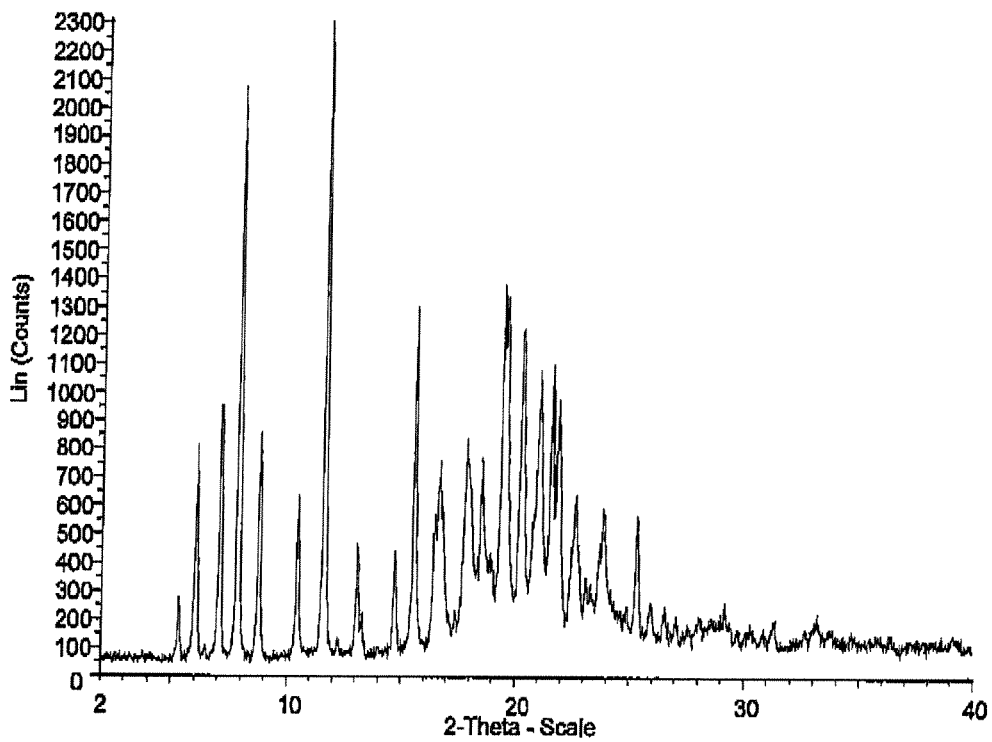
| 2-theta | d-spacing | Relative Intensities |
|---|---|---|
| 6.0 | 14.7 | 35 |
| 7.0 | 12.6 | 41 |
| 7.8 | 11.3 | 90 |
| 8.7 | 10.1 | 37 |
| 10.4 | 8.5 | 27 |
| 11.6 | 7.6 | 100 |
| 13.0 | 6.8 | 20 |
| 14.7 | 6.0 | 19 |
| 15.5 | 5.7 | 56 |
| 20.2 | 4.4 | 53 |

Figure 4: n-hexyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate
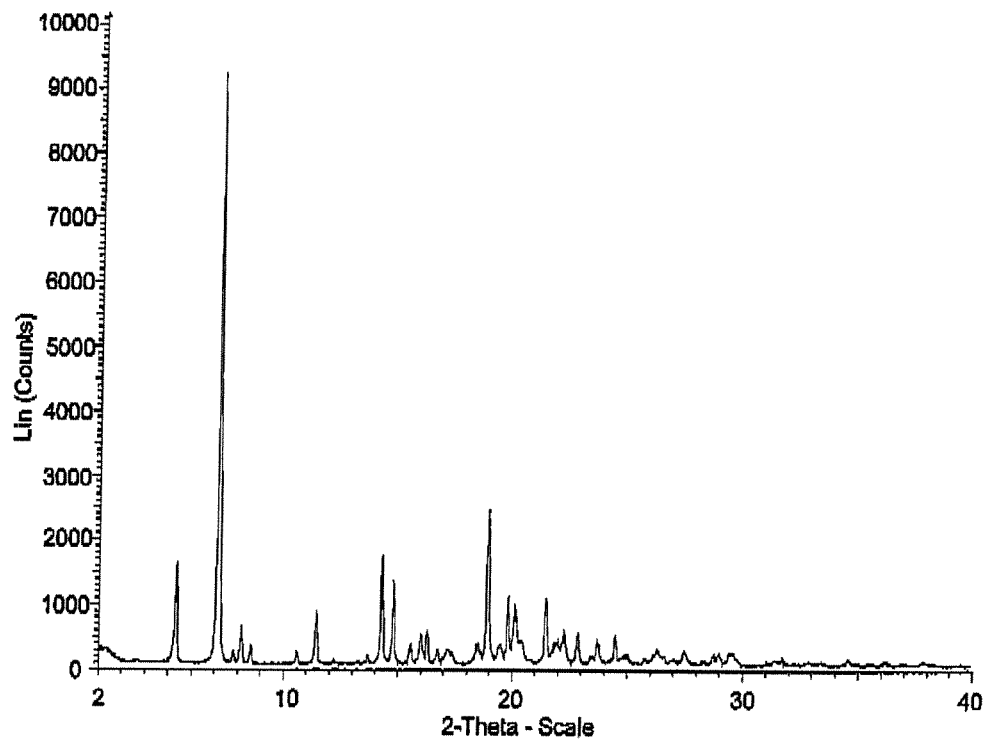
| 2-theta | d-spacing | Relative Intensities |
|---|---|---|
| 5.3 | 16.8 | 18 |
| 7.1 | 12.4 | 100 |
| 11.4 | 7.8 | 10 |
| 14.2 | 6.2 | 19 |
| 14.8 | 6.0 | 14 |
| 18.9 | 5.7 | 27 |
| 20.1 | 4.4 | 10 |
| 20.4 | 4.4 | 5 |
| 21.4 | 4.1 | 12 |

Figure 5: Ethyl-(E)-7-[4-(4-fluorophenyl)-6-isopropyl-2-[methyl(methylsulfonyl)amino]pyrimidin-5-yl](3R,5S)-3,5-dihydroxyhept-6-enoate
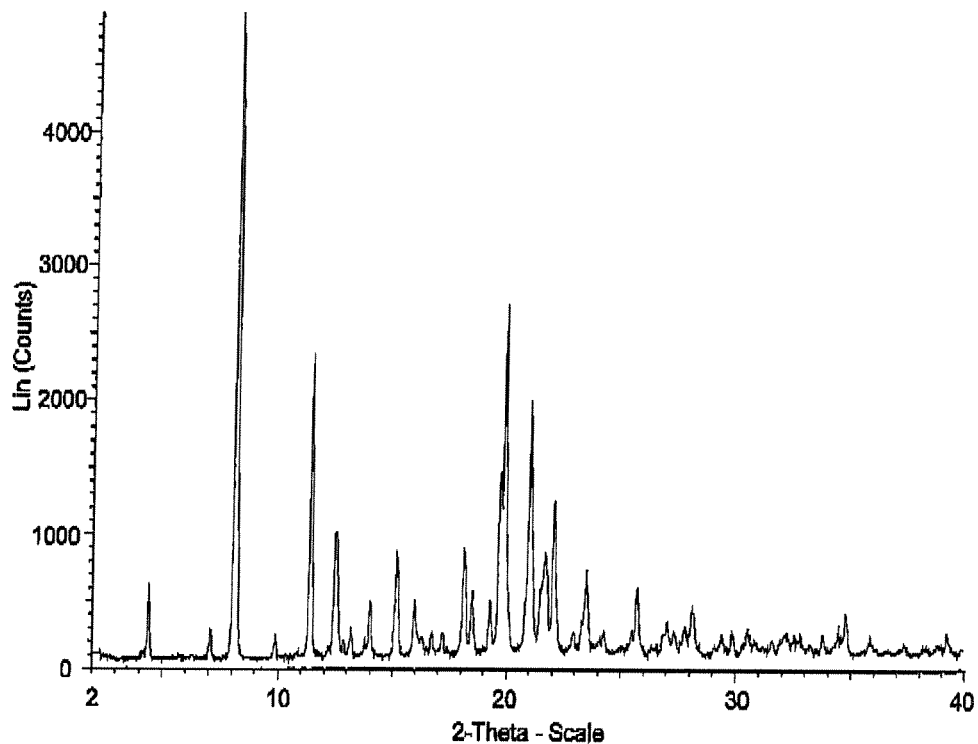
| 2-theta | d-spacing | Relative Intensities |
|---|---|---|
| 4.3 | 20.4 | 13 |
| 8.1 | 11.0 | 100 |
| 11.3 | 7.8 | 48 |
| 12.4 | 7.1 | 21 |
| 15.1 | 5.9 | 18 |
| 19.9 | 4.5 | 56 |
| 21.0 | 4.2 | 41 |
| 21.7 | 4.1 | 18 |
| 22.1 | 4.0 | 26 |
| 23.5 | 3.8 | 15 |

Figure 6: iso-Propyl-(E)-7-[4-(4-fluorophenyl)-6-isopropyl-2-[methyl(methylsulfonyl)amino]pyrimidin-5-yl](3R,5S)-3,5-dihydroxyhept-6-enoate
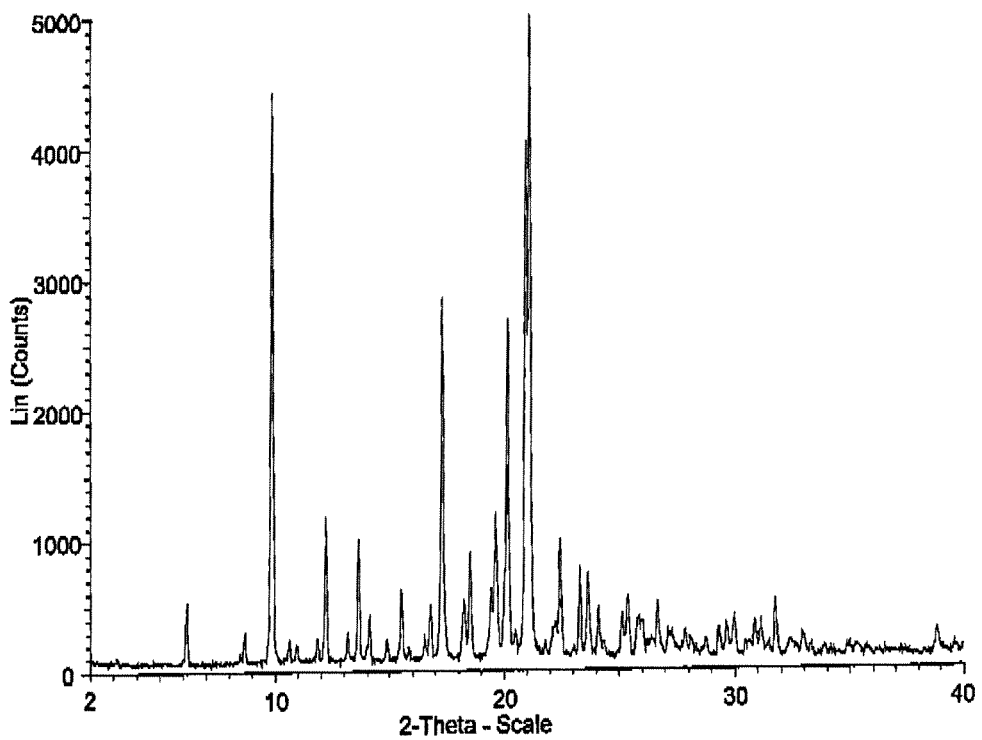
| 2-theta | d-spacing | Relative Intensities |
|---|---|---|
| 9.8 | 9.0 | 88 |
| 12.2 | 7.3 | 24 |
| 13.6 | 6.5 | 20 |
| 17.3 | 5.1 | 57 |
| 18.5 | 4.8 | 18 |
| 19.6 | 4.5 | 24 |
| 20.1 | 4.4 | 53 |
| 21.1 | 4.2 | 100 |
| 22.4 | 4.0 | 20 |
| 23.3 | 3.8 | 16 |

Figure 7: tert-Butyl-(E)-7-[4-(4-fluorophenyl)-6-isopropyl-2-methyl(methylsulfonyl)amino]pyrimidin-5-yl](3R,5S)-3,5-dihydroxyhept-6-enoate
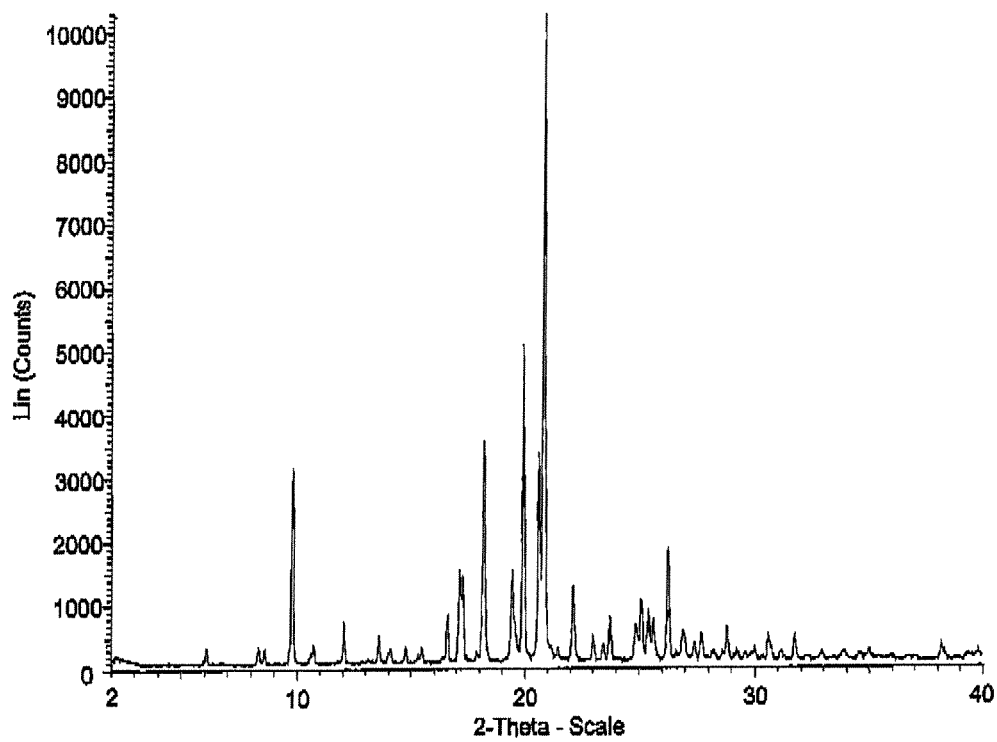
| 2-theta | d-spacing | Relative Intensities |
|---------|-----------|----------------------|
| 9.8 | 9.1 | 31 |
| 17.2 | 5.2 | 13 |
| 18.2 | 4.9 | 35 |
| 19.4 | 4.6 | 15 |
| 19.9 | 4.5 | 50 |
| 20.6 | 4.3 | 33 |
| 20.8 | 4.3 | 100 |
| 22.1 | 4.0 | 12 |
| 25.1 | 3.5 | 10 |
| 26.3 | 3.4 | 18 |

Figure 8: (*E*)-7-[4-(4-fluorophenyl)-6-isopropyl-2-[methyl(methylsulfonyl)amino]pyrimidin-5-yl](3*R*,5*S*)-3,5-dihydroxyhept-6-enoic acid-(3,6)-lactone
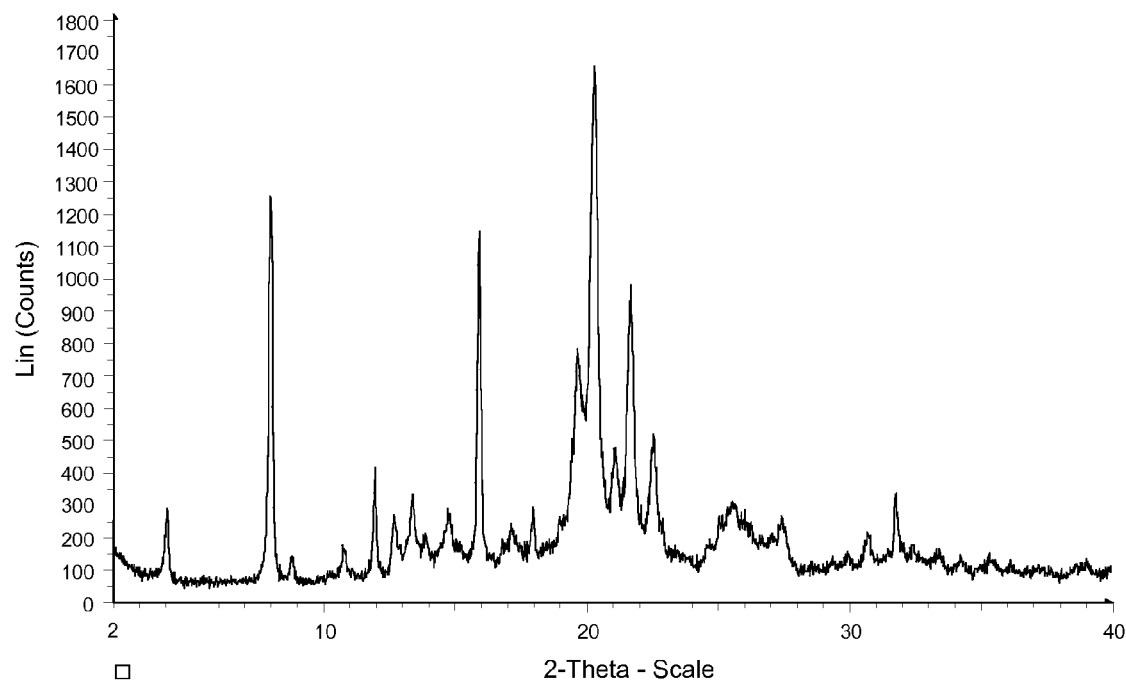
| 2-theta | d-spacing | Relative Intensities |
|---------|-----------|----------------------|
| 7.9 | 11.1 | 76 |
| 11.9 | 7.4 | 25 |
| 15.9 | 5.6 | 69 |
| 20.3 | 4.4 | 100 |
| 21.7 | 4.1 | 59 |
| 22.5 | 3.9 | 31 |

PROCESS FOR THE MANUFACTURE OF THE CALCIUM SALT OF ROSUVASTATIN (E)-7-[4-(4-FLUOROPHENYL)-6-ISOPROPYL-2-[METHYL(METHYLSULFONYL)AMINO]-PYRIMIDIN-5-YL](3R,5S)-3,5-DIHYDROXYHEPT-6-ENOIC ACID AND CRYSTALLINE INTERMEDIATES THEREOF

This application is a Divisional application of copending U.S. application Ser. No. 10/576,774, filed Mar. 16, 2007, which is a U.S. National Phase application of International application No. PCT/GB2004/004481, filed Oct. 22, 2004, which claims the benefit of Great Britain patent application No. 0324791.3, filed Oct. 24, 2003, all of which are herein incorporated by reference in their entireties.

This invention concerns improvements to a chemical process, particularly a chemical process for manufacture of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt (1) (illustrated below), which is useful for the production of a pharmaceutical useful in the treatment of, inter alia, hypercholesterolemia, hyperlipoproteinemia and atherosclerosis. This invention also concerns crystalline intermediates useful in the chemical process.

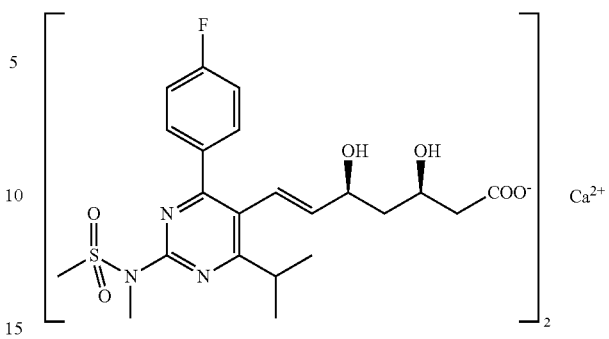

The sodium salt (3) and calcium salt (1) of the compound (E)-7-[4-(4-fluorophenyl)-6-isopropyl-2-[methyl(methylsulfonyl)amino]pyrimidin-5-yl](3R,5S)-3,5-dihydroxyhept-6-enoic acid (hereinafter referred to as the 'Agent') were disclosed in European patent 0521471. This patent also describes a process for the synthesis of the calcium salt (1), via the dihydroxy ester (2) and the sodium salt (3), as shown in Scheme 1 below. The calcium salt thus formed is then collected and dried and may be processed further as required.

Scheme 1

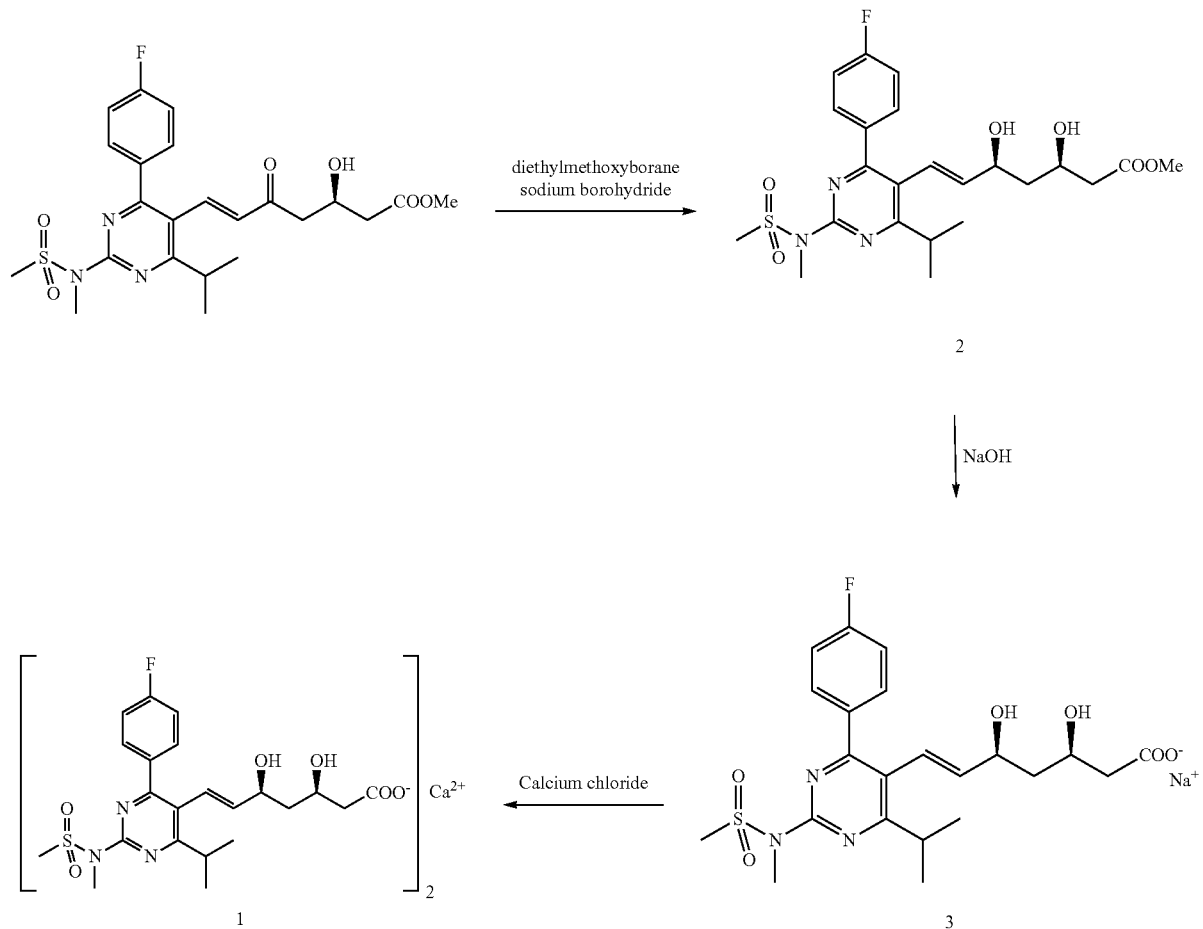

Our International patent application WO 00/49014 describes an alternative route to the calcium salt (1), also via the sodium salt (3), from the compound tert-butyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate (BEM) (4), which is exemplified as shown in Scheme 2 below:

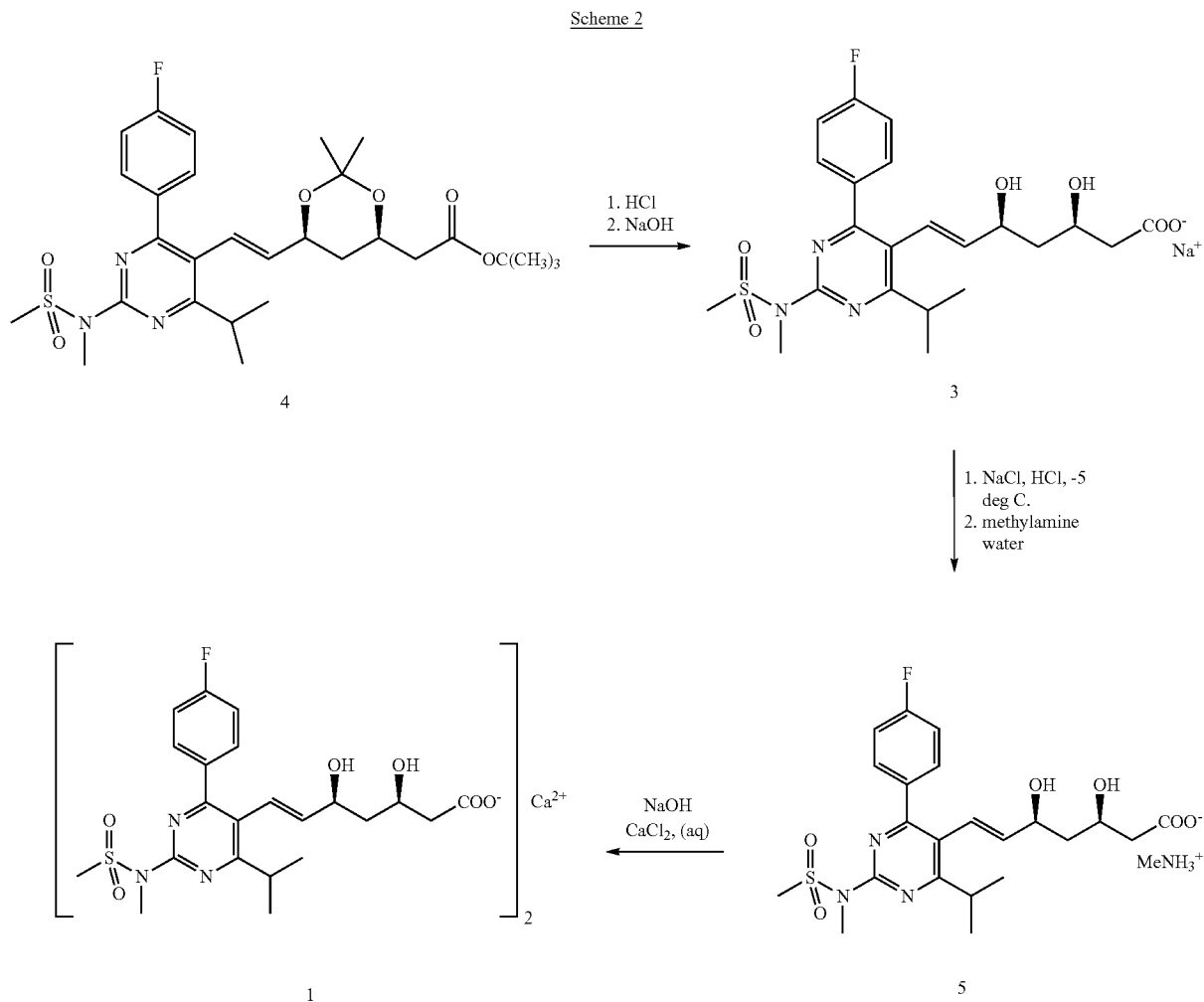

As described in WO 00/49014, the transformation from BEM (4) to the calcium salt (1) may be carried out via the methylamine salt (5) as shown in Scheme 2. Isolation of this intermediate crystalline methylamine salt allows purification by recrystallisation before final formation of the (amorphous) calcium salt. However formation of the methylamine salt introduces an extra step into the process, which is generally undesirable for manufacture (for example because of additional cost and the potential for introduction of additional impurities).

The transformation from BEM (4) to the sodium salt (3) in Scheme 2 takes place in two steps as shown below in Scheme 3.

Scheme 3

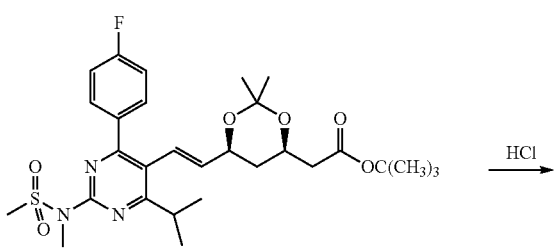

-continued

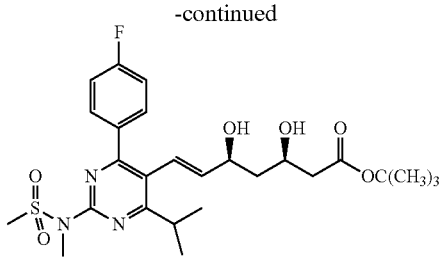
6

↓ NaOH

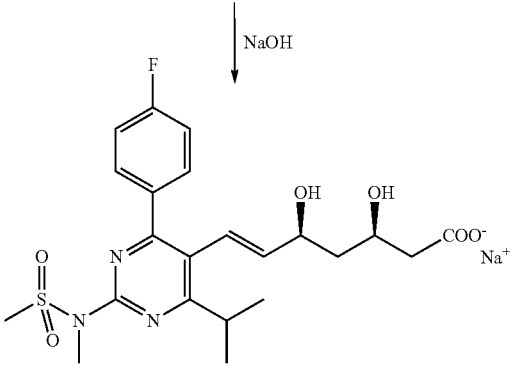
3

Treatment with hydrochloric acid hydrolyses the acetal to the diol (6) (referred to herein as BED), then treatment with sodium hydroxide hydrolyses the ester to give the sodium salt (3) of the parent carboxylic acid. The intermediate compound BED (6) is not isolated in the process described in WO 00/49014. The analogous methyl ester (2) was described in European patent 0521471 as a syrup and therefore, by analogy, isolation of BED (6) would not be expected to provide any advantages to the process.

However we have surprisingly found that BED and other (1-6C)alkyl ester analogues are generally crystalline compounds which may advantageously be isolated and recrystallised, thus removing the need for isolation of an intermediate salt such as the methylamine salt in order for purification to be carried out.

Therefore the present invention provides a process for the manufacture of the calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid, comprising:
a) acid hydrolysis of an acetal protecting group in a compound of the formula (7)

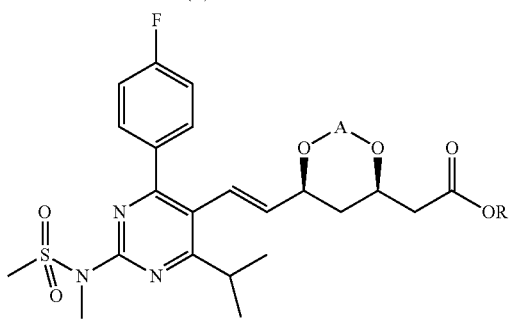
7 wherein A is an acetal or ketal protecting group and R is (1-6C)alkyl, and isolation of the resulting crystalline compound of the formula (8);

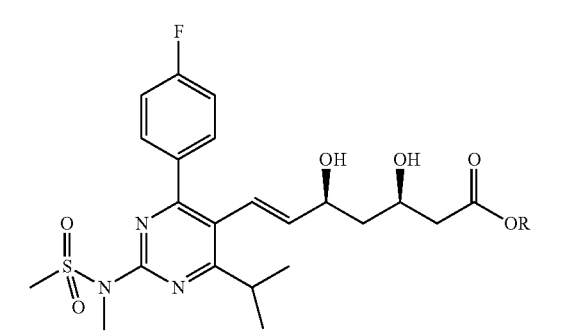
8 b) optional recrystallisation of the compound of the formula (8);
c) hydrolysis of the ester group in the compound (8) to give a dihydroxy carboxylate derivative (9) (wherein M is hydrogen or a metal counterion other than calcium) or a compound of the formula (1); and

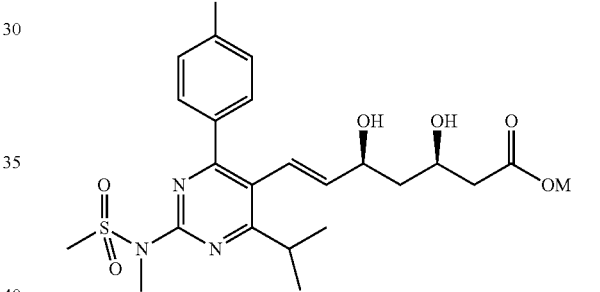
9 d) where necessary, conversion of a compound of the formula (9) into a compound of the formula (1).

In a further aspect of the invention there is provided crystalline compounds of the formula (8).

Furthermore, we have found that some compounds of the formula (7), which are analogues of BEM (4) are also crystalline and are themselves useful intermediates which may be recrystallised if necessary to improve the quality of the material. These crystalline compounds are novel and each independently provides a further aspect of the invention.

Thus in a further aspect of the invention is provided crystalline methyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=9.5, 13.6 and 17.5.

In a further aspect of the invention is provided crystalline methyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=5.7, 9.5, 13.6, 17.5, 19.9 and 22.4.

In a further aspect of the invention is provided crystalline methyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=5.7, 8.7, 9.5, 13.6, 17.5, 19.0, 19.9, 20.8, 21.8 and 22.4.

In a further aspect of the invention is provided crystalline methyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern substantially as shown in FIG. 1.

In a further aspect of the invention is provided crystalline ethyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=15.9, 18.4 and 19.5.

In a further aspect of the invention is provided crystalline ethyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=15.9, 18.4, 19.5, 23.0, 24.3 and 25.0.

In a further aspect of the invention is provided crystalline ethyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=5.9, 8.0, 12.2, 15.9, 18.4, 19.5, 19.7, 23.0, 24.3 and 25.0.

In a further aspect of the invention is provided crystalline ethyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern substantially as shown in FIG. 2.

In a further aspect of the invention is provided crystalline iso-propyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=7.8, 11.6 and 15.5.

In a further aspect of the invention is provided crystalline iso-propyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=6.9, 7.0, 7.8, 8.7, 11.6 and 15.5.

In a further aspect of the invention is provided crystalline iso-propyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=6.9, 7.0, 7.8, 8.7, 10.4, 11.6, 13.0, 14.7, 15.5 and 20.2.

In a further aspect of the invention is provided crystalline iso-propyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern substantially as shown in FIG. 3.

In a further aspect of the invention is provided crystalline n-hexyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=5.3, 7.1 and 18.9.

In a further aspect of the invention is provided crystalline n-hexyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=5.3, 7.1, 14.2, 14.8, 18.9 and 21.4.

In a further aspect of the invention is provided crystalline n-hexyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern with peaks at 2-theta=5.3, 7.1, 11.4, 14.2, 14.8, 18.9, 20.1, 20.4 and 21.4.

In a further aspect of the invention is provided crystalline n-hexyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate having an X-ray powder diffraction pattern substantially as shown in FIG. 4.

In a further aspect of the invention is provided crystalline ethyl-(E)-7-[4-(4-fluorophenyl)-6-isopropyl-2-[methyl(methylsulfonyl)amino]pyrimidin-5-yl](3R,5S)-3,5-dihydroxy-hept-6-enoate having an X-ray powder diffraction pattern with peaks at 2-theta=8.1, 11.3 and 19.9.

In a further aspect of the invention is provided crystalline ethyl-(E)-7-[4-(4-fluorophenyl)-6-isopropyl-2-[methyl(methylsulfonyl)amino]pyrimidin-5-yl](3R,5S)-3,5-dihydroxy-hept-6-enoate having an X-ray powder diffraction pattern with peaks at 2-theta=8.1, 11.3, 12.4, 19.9, 21.0 and 22.1.

In a further aspect of the invention is provided crystalline ethyl-(E)-7-[4-(4-fluorophenyl)-6-isopropyl-2-[methyl(methylsulfonyl)amino]pyrimidin-5-yl](3R,5S)-3,5-dihydroxy-hept-6-enoate having an X-ray powder diffraction pattern with peaks at 2-theta=4.3, 8.1, 11.3, 12.4, 15.1, 19.9, 21.0, 21.7, 22.1 and 23.5.

In a further aspect of the invention is provided crystalline ethyl-(E)-7-[4-(4-fluorophenyl)-6-isopropyl-2-[methyl(methylsulfonyl)amino]pyrimidin-5-yl](3R,5S)-3,5-dihydroxy-hept-6-enoate having an X-ray powder diffraction pattern substantially as shown in FIG. 5.

In a further aspect of the invention is provided crystalline iso-propyl-(E)-7-[4-(4-fluorophenyl)-6-isopropyl-2-[methyl(methylsulfonyl)amino]pyrimidin-5-yl](3R,5S)-3,5-dihydroxyhept-6-enoate having an X-ray powder diffraction pattern with peaks at 2-theta=9.8, 17.3 and 21.1.

In a further aspect of the invention is provided crystalline iso-propyl-(E)-7-[4-(4-fluorophenyl)-6-isopropyl-2-[methyl(methylsulfonyl)amino]pyrimidin-5-yl](3R,5S)-3,5-dihydroxyhept-6-enoate having an X-ray powder diffraction pattern with peaks at 2-theta=9.8, 12.2, 17.3, 19.6, 20.1 and 21.1.

In a further aspect of the invention is provided crystalline iso-propyl-(E)-7-[4-(4-fluorophenyl)-6-isopropyl-2-[methyl(methylsulfonyl)amino]pyrimidin-5-yl](3R,5S)-3,5-dihydroxyhept-6-enoate having an X-ray powder diffraction pattern with peaks at 2-theta=9.8, 12.2, 13.6, 17.3, 18.5, 19.6, 20.1, 21.1, 22.4 and 23.3.

In a further aspect of the invention is provided crystalline iso-propyl-(E)-7-[4-(4-fluorophenyl)-6-isopropyl-2-[methyl(methylsulfonyl)amino]pyrimidin-5-yl](3R,5S)-3,5-dihydroxyhept-6-enoate having an X-ray powder diffraction pattern substantially as shown in FIG. 6.

In a further aspect of the invention is provided crystalline tert-butyl-(E)-7-[4-(4-fluorophenyl)-6-isopropyl-2-[methyl(methylsulfonyl)amino]pyrimidin-5-yl](3R,5S)-3,5-dihydroxyhept-6-enoate having an X-ray powder diffraction pattern with peaks at 2-theta=18.2, 19.9 and 20.8.

In a further aspect of the invention is provided crystalline tert-butyl-(E)-7-[4-(4-fluorophenyl)-6-isopropyl-2-[methyl(methylsulfonyl)amino]pyrimidin-5-yl](3R,5S)-3,5-dihydroxyhept-6-enoate having an X-ray powder diffraction pattern with peaks at 2-theta=9.8, 18.2, 19.9, 20.6, 20.8 and 26.3.

In a further aspect of the invention is provided crystalline tert-butyl-(E)-7-[4-(4-fluorophenyl)-6-isopropyl-2-[methyl(methylsulfonyl)amino]pyrimidin-5-yl](3R,5S)-3,5-dihydroxyhept-6-enoate having an X-ray powder diffraction pattern with peaks at 2-theta=9.8, 17.4, 18.2, 19.4, 19.9, 20.6, 20.8, 22.1, 25.1 and 26.3.

In a further aspect of the invention is provided crystalline tert-butyl-(E)-7-[4-(4-fluorophenyl)-6-isopropyl-2-[methyl (methylsulfonyl)amino]pyrimidin-5-yl](3R,5S)-3,5-dihydroxyhept-6-enoate having an X-ray powder diffraction pattern substantially as shown in FIG. 7.

BRIEF DESCRIPTION OF THE DRAWINGS

FIG. 1 shows an XRPD trace for Methyl (E)-(6-{2-[4-(4-fluorophenyl)-6-isopropyl-2-[methyl(methylsulfonyl) amino]pyrimidin-5-yl]vinyl}(4R,6S)-2,2-dimethyl[1,3]dioxan-4-yl)acetate.

FIG. 2 shows an XRPD trace for Ethyl (E)-(6-{2-[4-(4-fluorophenyl)-6-isopropyl-2-[methyl(methylsulfonyl) amino]pyrimidin-5-yl]vinyl}(4R,6S)-2,2-dimethyl[1,3]dioxan-4-yl)acetate.

FIG. 3 shows an XRPD trace for iso-Propyl (E)-(6-{2-[4-(4-fluorophenyl)-6-isopropyl-2-[methyl(methylsulfonyl) amino]pyrimidin-5-yl]vinyl}(4R,6S)-2,2-dimethyl[1,3]dioxan-4-yl)acetate.

FIG. 4 shows an XRPD trace for n-Hexyl (E)-(6-{2-[4-(4-fluorophenyl)-6-isopropyl-2-[methyl(methylsulfonyl) amino]pyrimidin-5-yl]vinyl}(4R,6S)-2,2-dimethyl[1,3]dioxan-4-yl)acetate.

FIG. 5 shows an XRPD trace for Ethyl-(E)-7-[4-(4-fluorophenyl)-6-isopropyl-2-[methyl(methylsulfonyl)amino]pyrimidin-5-yl](3R,5S)-3,5-dihydroxyhept-6-enoate.

FIG. 6 shows an XRPD trace for iso-Propyl-(E)-7-[4-(4-fluorophenyl)-6-isopropyl-2-[methyl(methylsulfonyl) amino]pyrimidin-5-yl](3R,5S)-3,5-dihydroxyhept-6-enoate.

FIG. 7 shows an XRPD trace for tert-Butyl-(E)-7-[4-(4-fluorophenyl)-6-isopropyl-2-[methyl(methylsulfonyl) amino]pyrimidin-5-yl](3R,5S)-3,5-dihydroxyhept-6-enoate.

FIG. 8 shows an XRPD trace for (E)-7-[4-(4-fluorophenyl)-6-isopropyl-2-[methyl(methylsulfonyl)amino]pyrimidin-5-yl](3R,5S)-3,5-dihydroxyhept-6-enoic acid-(3-6-lactone.

A crystalline polymorph of BEM (4) is provided as a further aspect of the invention.

The X-ray powder diffraction spectra were determined by mounting a sample of the crystalline form on Siemans single silicon crystal (SSC) wafer mounts and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms. The collimated x-ray source was passed through an automatic variable divergence slit set at V20 (20 mm path length) and the reflected radiation directed through a 2 mm antiscatter slit and a 0.2 mm detector slit. The sample was exposed for 4 seconds per 0.02 degree 2-theta increment (continuous scan mode) over the range 2 degrees to 40 degrees 2-theta in theta-theta mode. The running time was 2 hours 6 minutes and 40 seconds. The instrument was equipped with a scintillation counter as detector. Control and data capture was by means of a DECpc LPv 433sx personal computer running with Diffrac AT (Socabim) software.

It will be understood that the 2-theta values of an X-ray powder diffraction pattern may vary slightly from one machine to another or from one sample to another, and so the values quoted are not to be construed as absolute. It will also be understood that the relative intensities of peaks may vary according to the orientation of the sample under test so that the intensities in the XRD traces included herein are illustrative and not intended to be used for absolute comparison.

The crystalline forms obtained according to the present invention are substantially free from other crystal and non-crystal forms of each compound of the formula 7 or 8. The term "substantially free from other crystal and non-crystal forms" shall be understood to mean that the desired crystal form contains less than 50%, preferably less than 10%, more preferably less than 5% of any other form of the compound.

Suitable values for the acetal protecting group A are as described in EP0319847. A preferred value for A is isopropylidene such that the compound of the formula (7) is a compound of the formula (7a).

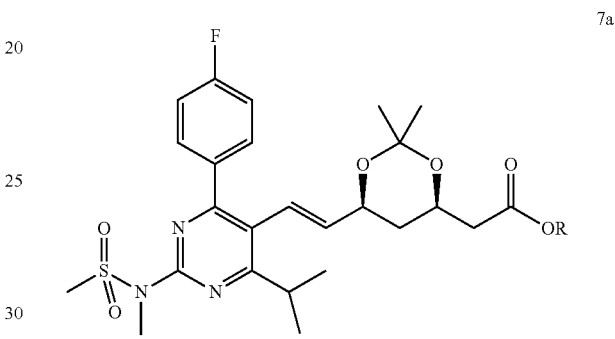

7a

Conveniently, in compounds of the formulae 7, 7a and 8, R is (2-6C)alkyl. More conveniently, R is (2-5C)alkyl.

Suitably R is selected from methyl, ethyl, propyl, isopropyl, butyl, tert-butyl, pentyl and n-hexyl.

Preferably R is selected from methyl, ethyl, iso-propyl, tert-butyl and n-hexyl.

More preferably R is selected from ethyl, iso-propyl and tert-butyl.

In a further aspect of the invention there is provided a process for the manufacture of the calcium salt of (E)-7-[4-(4-fluorophenyl)-6-isopropyl-2-[methyl(methylsulfonyl) amino]pyrimidin-5-yl](3R,5S)-3,5-dihydroxyhept-6-enoic acid, comprising:

a) acid hydrolysis of an acetal protecting group in a compound of the formula (7a)

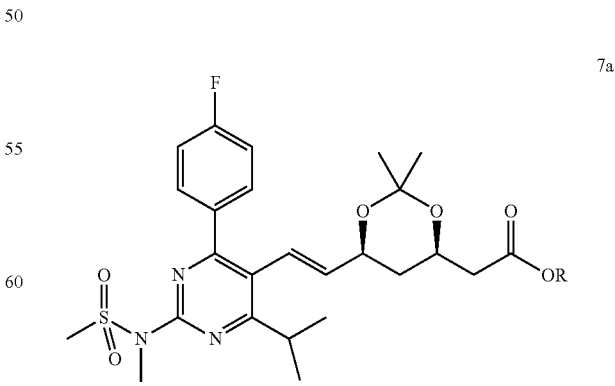

7a wherein R is ethyl, iso-propyl or tert-butyl, and isolation of the resulting crystalline compound of the formula (8);

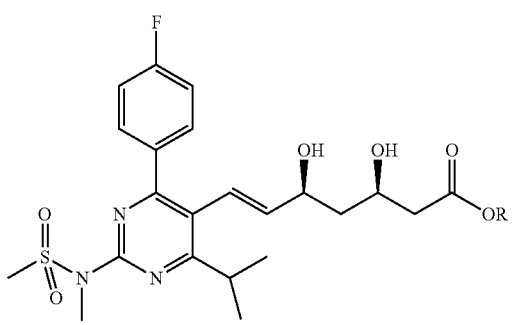

8 b) optional recrystallisation of the compound of the formula (8);

c) hydrolysis of the ester group in the compound (8) to give a dihydroxy carboxylate derivative (9) (wherein M is hydrogen or a metal counterion other than calcium) or a compound of the formula (1); and

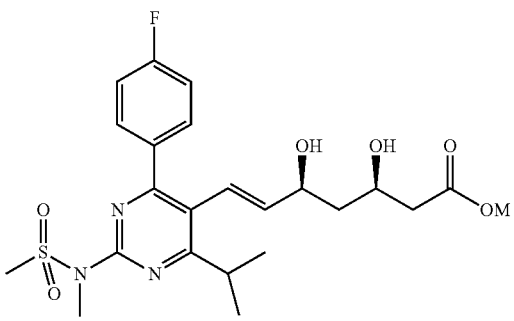

9 d) where necessary, conversion of a compound of the formula (9) into a compound of the formula (1).

In a further aspect of the invention there is provided a process for the manufacture of the calcium salt of (E)-7-[4-(4-fluorophenyl)-6-isopropyl-2-[methyl(methylsulfonyl) amino]pyrimidin-5-yl](3R,5S)-3,5-dihydroxyhept-6-enoic acid, comprising:

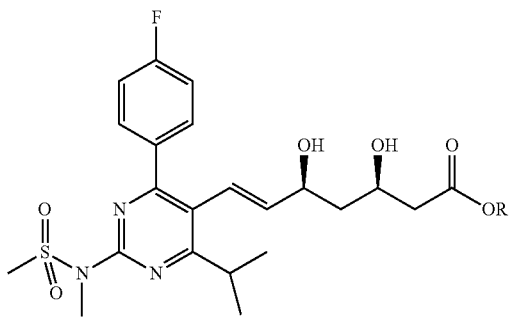

8 a) hydrolysis of the ester group in a crystalline compound of the formula (8) (where R is as hereinbefore defined) to give a dihydroxy carboxylate derivative (9) (wherein M is hydrogen or a metal counterion other than calcium) or a compound of the formula (1); and

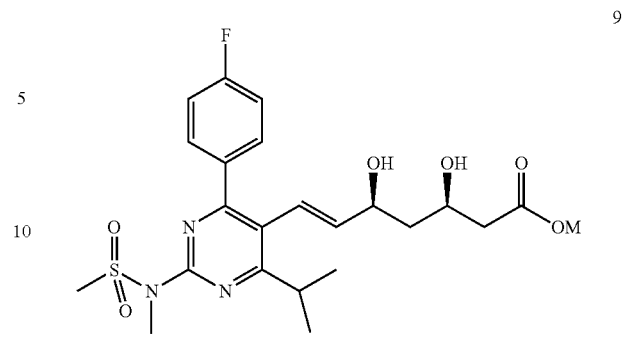

9 b) where necessary, conversion of a compound of the formula (9) into a compound of the formula (1).

The compound of the formula (8) in this aspect of the invention may be made by any convenient method such as those described and referenced hereinbefore.

In a further aspect of the invention, there is provided the use of a crystalline compound of formula (7a) as an intermediate in the manufacture of amorphous bis[(RE)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt.

In a further aspect of the invention, there is provided the use of a crystalline compound of formula (8) as an intermediate in the manufacture of amorphous bis[(RE)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt.

Under some conditions for the hydrolysis of the acetal group A in a compound of formula (7), the group R may also simultaneously be hydrolysed which may result in formation of the crystalline lactone (10) [(E)-7-[4-(4-fluorophenyl)-6-isopropyl-2-[methyl(methylsulfonyl)amino]pyrimidin-5-yl](3R,5S)-3,5-dihydroxyhept-6-enoic acid-(3,6)-lactone; also described as N-(4-(4-fluorophenyl)-5-{(E)-2-[{2S,4R)-4-hydroxy-6-oxotetrahydro-2H-pyran-2-yl]ethenyl}-6-isopropylpyrimidin-2-yl)-N-methylmethanesulfonamide]. This compound is hereinafter described as "lactone".

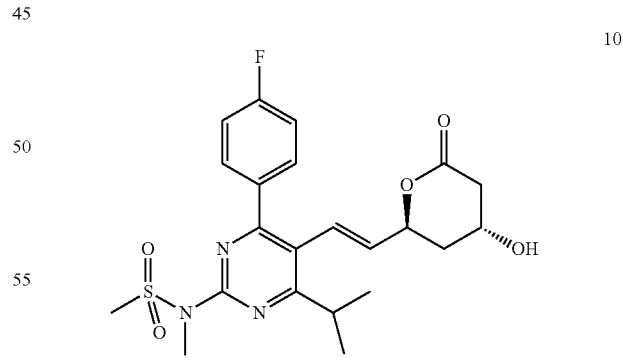

10

Suitable conditions for conversion of compounds of formula (7), for example (7a), into a compound of formula (10) are, for example, treatment with aqueous acid (such as hydrochloric acid) and removal of water by azeotropic distillation of toluene or MTBE (methyl tert-butyl ether). The crystalline lactone (10) may be isolated instead of the compound (8) and then converted into a compound of the formula (9) or formula (I) by hydrolysis in aqueous base.

Therefore in a further aspect of the invention there is provided a process for the manufacture of the calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid, comprising:

a) acid hydrolysis of an acetal protecting group in a compound of the formula (7)

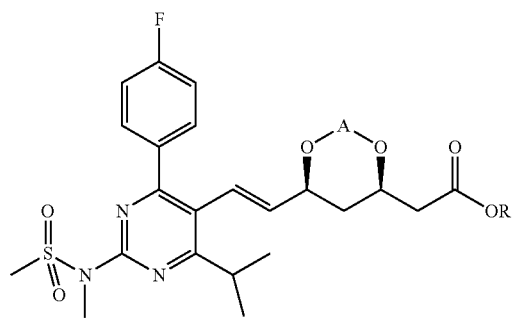

wherein A is an acetal or ketal protecting group and R is (1-6C)alkyl, and isolation of the resulting crystalline compound of the formula (10);

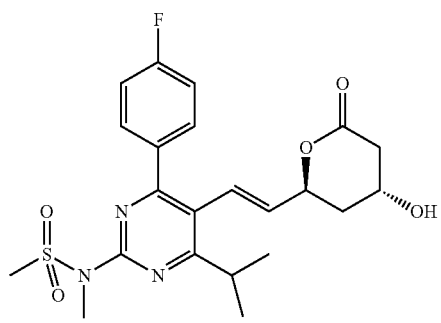

b) optional recrystallisation of the compound of the formula (10);
c) hydrolysis of the compound of formula (10) to give a dihydroxy carboxylate derivative (9) (wherein M is a metal counterion other than calcium) or a compound of the formula (1); and

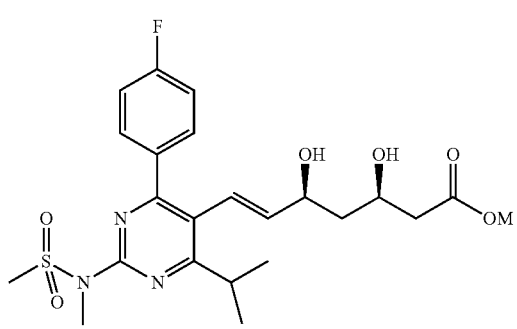

d) where necessary, conversion of a compound of the formula (9) into a compound of the formula (1).

Preferably step c) is carried out by hydrolysis in aqueous base, such as alkali metal bases, for example sodium hydroxide (M is Na), or potassium hydroxide (M is K).

In a further aspect of the invention there is provided a process for the manufacture of the calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid, comprising:

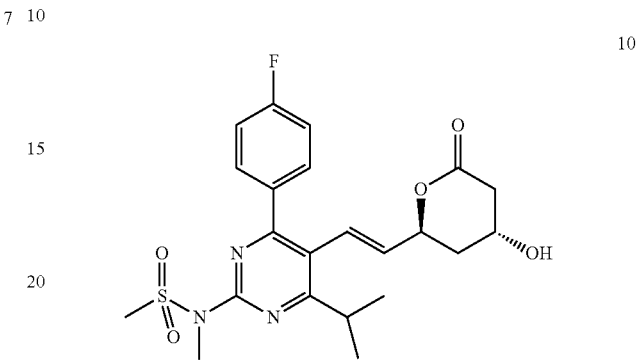

a) hydrolysis of the ester group in a crystalline compound of the formula (10) to give a dihydroxy carboxylate derivative (9) (wherein M is a metal counterion other than calcium) or a compound of the formula (1); and

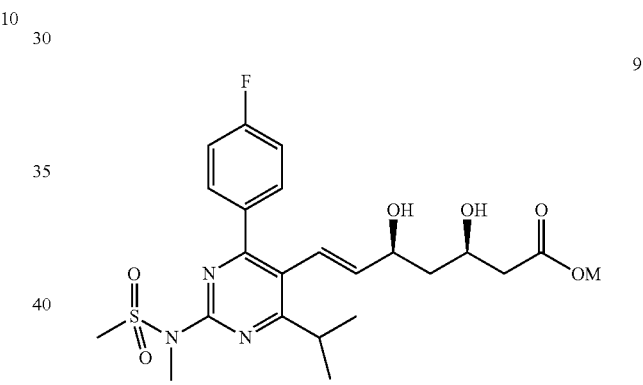

b) where necessary, conversion of a compound of the formula (9) into a compound of the formula (1).

In a further aspect of the invention is provided crystalline (E)-7-[4-(4-fluorophenyl)-6-isopropyl-2-[methyl(methylsulfonyl)amino]pyrimidin-5-yl](3R,5S)-3,5-dihydroxyhept-6-enoic acid-(3,6)-lactone having an X-ray powder diffraction pattern with peaks at 2-theta=7.9, 15.9 and 20.3.

In a further aspect of the invention is provided crystalline (E)-7-[4-(4-fluorophenyl)-6-isopropyl-2-[methyl(methylsulfonyl)amino]pyrimidin-5-yl](3R,5S)-3,5-dihydroxyhept-6-enoic acid-(3,6)-lactone having an X-ray powder diffraction pattern with peaks at 2-theta=7.9, 11.9, 15.9, 20.3, 21.7 and 22.5.

In a further aspect of the invention is provided crystalline (E)-7-[4-(4-fluorophenyl)-6-isopropyl-2-[methyl(methylsulfonyl)amino]pyrimidin-5-yl](3R,5S)-3,5-dihydroxyhept-6-enoic acid-(3,6)-lactone having an X-ray powder diffraction pattern substantially as shown in FIG. 8.

It will be appreciated that the process described in WO 00/49014 for isolation of the amorphous calcium salt of the Agent, or the process described in WO2004/014872, for precipitation of the amorphous form of the calcium salt of the Agent from a (substantially) aqueous solution of a different salt form, will generally lead to a proportion of residual calcium salt of the Agent in waste solutions such as the mother liquors remaining after the precipitated salt has been filtered off. Even a very small proportion of such residue may represent significant financial loss if the process is carried out repeatedly on a commercial manufacturing scale. Any reduction in such residue also potentially provides environmental benefits, reducing the amount of treatment that effluent requires before it can be disposed of.

We have found that this loss may be avoided by treatment of said waste solutions (such as mother liquors) such that the residue calcium salt of the Agent may be isolated as crystalline lactone, optionally re-crystallised and then re-treated to form the desired calcium salt of the Agent. Thus lactone has value as a processing aid for isolation of the amorphous form of the Agent.

Therefore in a further aspect of the invention, there is provided a process for formation of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt comprising isolation of crystalline (E)-7-[4-(4-fluorophenyl)-6-isopropyl-2-[methyl(methylsulfonyl)amino]pyrimidin-5-yl](3R,5S)-3,5-dihydroxyhept-6-enoic acid-(3,6)-lactone from a solution and subsequent conversion to the amorphous form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt.

In a further aspect of the invention, there is provided the use of lactone (as hereinbefore defined) as a processing aid for isolation of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt.

In a further aspect of the invention, there is provided the use of lactone (as hereinbefore defined) as a processing aid for recovery of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt from waste solutions.

In a further aspect of the invention, there is provided the use of lactone (as hereinbefore defined) as an intermediate in the manufacture of amorphous bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt.

MTBE may be used to isolate crystalline lactone from waste solutions such as mother liquors. MTBE is also a suitable recrystallisation solvent for lactone.

The utility of the compound of the formula (I) formed by the process of the invention may be demonstrated by standard tests and clinical studies, including those described in EPA 521471.

A further aspect of the invention comprises a compound of the formula (I) obtained by the process of the invention as hereinbefore described.

A further aspect of the invention comprises a compound of the formula (I) obtainable by the process of the invention as hereinbefore described.

According to a further feature of the invention is a method of treating a disease condition wherein inhibition of HMG CoA reductase is beneficial which comprises administering to a warm-blooded mammal an effective amount of a compound of the formula (I) formed by the process of the invention. The invention also relates to the use of compounds of the formula (I) formed by the process of the invention in the manufacture of a medicament for use in a disease condition.

The compound of the invention may be administered to a warm-blooded animal, particularly a human, in need thereof for treatment of a disease in which HMG CoA reductase is implicated, in the form of a conventional pharmaceutical composition. Therefore in another aspect of the invention, there is provided a pharmaceutical composition comprising a compound of the formula (I) formed by the process of the invention in admixture with a pharmaceutically acceptable carrier.

Such compositions may be administered in standard manner for the disease condition that it is desired to treat, for example by oral, topical, parenteral, buccal, nasal, vaginal or rectal administration or by inhalation. For these purposes the compound of the formula (I) may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solution or suspensions or sterile emulsions. A preferred route of administration is oral. The compound of the formula (I) will be administered to humans at a daily dose in, for example, the ranges set out in EPA 521471. The daily doses may be given in divided doses as necessary, the precise amount received and the route of administration depending on the weight, age and sex of the patient being treated and on the particular disease condition being treated according to principles known in the art.

According to a further feature of the invention, there is provided a process for the manufacture of a pharmaceutical composition containing the compound of the formula (I) as active ingredient, which comprises admixing the compound of the formula (I) together with a pharmaceutically acceptable carrier.

The invention will now be illustrated by the following examples. $^1$H NMR were analysed using a Bruker DPX400 operating at a field strength of 400 MHz, and unless otherwise stated were run in deuterochloroform. Chemical shifts are given in parts per million relative to tetramethylsilane. Peak multiplicities are shown as: s=singlet, d=doublet, sept=septet, q=quartet, t=triplet, dd=doublet of doublets, dt=doublet of triplets, m=multiplet It will be appreciated that the crystalline compounds of formulae (7) and (8), and crystalline lactone, may additionally be characterised by other methods known in the art.

General Procedure for Synthesis of a Compound of Formula (7):

Example for R=iso-propyl: iso-Propyl(E)-(6-{2-[4(4 fluorophenyl)-6-isopropyl-2-[methyl (methylsulfonyl)amino]pyrimidin-5-yl]vinyl}(4R,6S)-2,2-dimethyl[1,3]dioxan-4-yl)acetate Sodium bis(trimethylsilyl)amide (80.47 mL, 1.0M in tetrahydrofuran (THF)) was added dropwise to a cooled solution of diphenyl[4-(4-fluorophenyl)-6-isopropyl-2-[methyl (methylsulfonyl)amino]pyrimidin-5-ylmethyl]phosphine oxide (40.43 g, 75 mmol) in THF (477.1 mL) at −65° C. over 30 minutes, maintaining the temperature at −65° C. Isopropyl-2-[(4R,6S)-6-formyl-2,2-dimethyl-1,3-dioxan-4-yl]acetate in toluene (21.68 g) was added dropwise to the solution over 35 minutes, maintaining the temperature at −65° C. The contents of the vessel were kept at −65° C. for 15 minutes, then allowed to warm evenly to 10° C. over 80 minutes. Water (40.4 mL) followed by acetic acid (6.87 g, 114 mmol) were added to give a two phase light yellow solution. The batch was then distilled at atmospheric pressure to remove ~485 mL of distillates. This solution was washed sequentially with water (84 mL), 7.0% w/w sodium bicarbonate (92.6 g), 1.8% w/w sodium bicarbonate (91.1 g) and water (63.5 mL). The resulting organic phase was distilled under vacuum at 270 mbar to leave ~95 mL of solution in the distillation flask (removing ~229 mL of distillates). Methanol (202 mL) at 50° C. was charged to the flask and the solution distilled at atmospheric pressure, removing ~134 mL of distillates. A further portion of methanol (229 mL) at 50° C. was added to the solution and the batch cooled to 40° C. over 30 minutes. The batch was cooled to 25° C. over 30 minutes, 0-5° C. over 30 minutes, then chilled to −8° C. over 20 minutes and kept at this temperature for 30 minutes. The solid was collected by vacuum filtration, washed with 2 portions of cooled (−8° C.) methanol (2×80.6 mL) then dried in a vacuum oven at 50° C., 200 mbar, yield=28.9 g (68.3%).

Analogues with different ester groups R may be made as above using the appropriate starting materials, with the following exceptions:

For the ethyl derivative: after the acetic acid quench the mixture was evaporated to dryness onto silica gel (Merck, 230-400 mesh) and added to a short plug of silica. Elution was performed with 25-27.5% ethyl acetate in iso-hexane. The isolated product was then crystallised from methanol (150 mL) as described in the method above.

For the methyl derivative, the crude product was evaporated to dryness onto silica after the first sodium bicarbonate treatment. Purification was performed on silica gel as for the ethyl derivative (eluting with 14, 16 and 20% ethyl acetate in iso-hexane). The product was crystallised from methanol.

Procedure for Compound of Formula 7 where R=n-Hexyl:

Sodium hydride (141 mg, 60% dispersion in mineral oil, 3.5 mmol) was added in one portion to n-hexanol (15 mL) at ambient temperature. After the resulting effervescence had stopped the clear solution was agitated for 30 minutes. N-Ethyl(E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate (2 g, 3.6 mmol) was added to the solution in one portion. After 90 minutes, acetic acid (263 mg, 3.6 mmol) was added to the reaction mixture and the solution left at ambient temperature for 16 hours. The solvent was removed on the rotary evaporater (oil pump) and then dissolved in ethyl acetate. The solution was evaporated to dryness onto silica and purified on silica eluting with 20% ethyl acetate in iso-hexane. The resulting pale yellow oil was crystallised from methanol as described above.

Analytical Data: for R-(E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate

| R | $^1$H NMR (ppm) |
|---|---|
| Iso-propyl | 1.15 (q, 1H), 1.24 (dd, 6H), 1.27 (dd, 6H), 1.40 (s, 3H), 1.49 (s, 3H), 1.55 (dt, 1H), 2.34 (dd, 1H), 2.50 (dd, 1H), 3.38 (spt, 1H), 3.51 (s, 3H), 3.57 (s, 3H), 4.32 (m, 1H), 4.43 (m, 1H), 5.04 (sptt, 1H), 5.47 (dd, 1H), 6.52 (d, 1H), 7.08 (t, 2H), 7.65 (dd, 2H) |
| Ethyl | 1.14 (q, 1H), 1.25-1.29 (m, 9H), 1.40 (s, 3H), 1.49 (s, 3H), 1.56 (dt, 1H), 2.37 (dd, 1H), 2.55 (dd, 1H), 3.38 (spt, 1H), 3.51 (s, 3H), 3.57 (s, 3H), 4.21-4.12 (m, 2H), 4.37-4.30 (m, 1H), 4.46-4.41 (m, 1H), 5.47 (dd, 1H), 6.53 (d, 1H), 7.08 (t, 2H), 7.65 (dd, 2H) |
| Methyl | 1.14 (q, 1H), 1.27 (dd, 6H), 1.40 (s, 3H), 1.49 (s, 3H), 1.56 (dt, 1H), 2.38 (dd, 1H), 2.57 (dd, 1H), 3.37 (spt, 1H), 3.51 (s, 3H), 3.57 (s, 3H), 3.70 (s, 3H), 4.37-4.30 (m, 1H), 4.46-4.41 (m, 1H), 5.47 (dd, 1H), 6.52 (d, 1H), 7.08 (t, 2H), 7.65 (dd, 2H) |
| n-Hexyl | 0.89 (t, 3H), 1.15 (q, 1H), 1.27 (dd, 6H), 1.37-1.29 (m, 7H), 1.40 (s, 3H), 1.49 (s, 3H), 1.66-1.57 (m, 2H), 2.38 (dd, 1H), 2.55 (dd, 1H), 3.37 (spt, 1H), 3.51 (s, 3H), 3.57 (s, 3H), 4.10 (t, 2H), 4.36-4.29 (m, 1H), 4.46-4.41 (m, 1H), 5.47 (dd, 1H), 6.52 (d, 1H), 7.08 (t, 2H), 7.65 (dd, 2H) |

General Procedure for Compounds of Formula (8):

Example for Iso-Propyl Analogue:

Hydrochloric acid (17.24 mL, 0.02M) was added dropwise over 100 minutes to a warm solution of iso-propyl(E)-7-[4-(4-fluorophenyl)-6-isopropyl-2-[methyl(methylsulfonyl)amino]pyrimidin-5-yl](3R,5S)-3,5-dihydroxyhept-6-enoate (10 g, 17 mmol) in acetonitrile (69 mL) at 35° C. The mixture was agitated for a further 80 minutes then allowed to cool to 25° C. over 30 minutes. Sodium chloride (9.26 g) in water (23 mL) was added to the mixture, which was agitated for 15 minutes then allowed to settle for 16 hours. The organic layer was separated off and the aqueous layer extracted with acetonitrile (15 mL). The combined organic layers were evaporated to dryness and the residue recrystallised from toluene (40 mL). The solid was dried in a vacuum oven at 40° C., 620 mbar, yield=7.06 g (79.3%).

Analogues with different ester groups R may be made as above with the following exceptions: for the ethyl derivative, the product did not crystallise from toluene: this solution was evaporated to dryness and purified on silica to afford an oily solid which was then treated with a 1:1 mixture of iso-hexane: toluene and filtered by vacuum filtration.

Analytical Data: for R-(E)-7-[4-(4-fluorophenyl)-6-isopropyl-2-[methyl(methylsulfonyl)amino]pyrimidin-5-yl](3R,5S)-3,5-dihydroxyhept-6-enoate

| R | $^1$H NMR (ppm) |
|---|---|
| t-Butyl | 1.27 (d, 6H), 1.42 (dt, 1H), 1.47 (s, 9H), 1.58-1.50 (m, 1H), 2.38 (d, 2H), 3.37 (spt, 1H), 3.51 (s, 3H), 3.57 (s, 3H), 3.65 (bs, 1H), 3.80 (bs, 1H), 4.18-4.15 (m, 1H), 4.48-4.44 (m, 1H), 5.46 (dd, 1H), 6.64 (d, 1H), 7.09 (t, 2H), 7.65 (dd, 2H) |
| Iso-propyl | 1.27-1.25 (m, 12H), 1.45 (dt, 1H), 1.60-1.51 (m, 1H), 2.43 (d, 2H), 3.37 (spt, 1H), 3.51 (s, 3H), 3.57 (s, 3H), 3.57 (bs, 1H), 3.73 (bs, 1H), 4.21-4.19 (m, 1H), 4.47-4.44 (m, 1H), 5.06 (spt, 1H), 5.46 (dd, 1H), 6.64 (d, 1H), 7.09 (t, 2H), 7.65 (dd, 2H) |
| Ethyl | 1.30-1.24 (m, 9H), 1.45 (dt, 1H), 1.60-1.52 (m, 1H), 2.46 (d, 2H), 3.37 (spt, 1H), 3.51 (s, 3H), 3.51 (bs, 1H), 3.57 (s, 3H), 3.70 (bs, 1H), 4.19 (q, 2H), 4.23-4.17 (m, 1H), 4.47-4.45 (m, 1H), 5.46 (dd, 1H), 6.64 (d, 1H), 7.09 (t, 2H), 7.65 (dd, 2H) |

Procedure for Formation of Lactone (3R,5S) (a)

(E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt (30.0 g) was dissolved in acetonitrile (300 mL) and saturated brine (50 mL) was added. The solution was then chilled to 0-5° C. The pH was adjusted to 4.0 with a mixture of 4N HCl (15 mL) and saturated brine (35 mL). An extra portion of water (15 mL) was added to dissolve the solid, resulting in two clear phases. The aqueous layer was separated off (112 mL) and the organic phase dried with magnesium sulphate. The solution was distilled at atmospheric pressure until ~100 mL of acetonitrile had been removed, then toluene (250 mL) was added gradually to maintain the distillation flask volume at 200 mL. This resulted in collecting ~390 mL of distillates at a final head temperature of 106° C. The solution was allowed to stir at ambient temperature overnight and was then heated to reflux for two hours. The mixture was cooled to 0-5° C. and the resulting solid was filtered, washed with toluene (2×20 mL) and dried at 35° C. under vacuum.

$^1$H NMR δ: 1.28-1.26 (m, 6H), 1.69-1.62 (m, 1H), 1.94-1.88 (m, 1H), 2.66-2.60 (m, 1H), 2.72 (dd, 1H), 3.33 (septet, 1H), 3.51 (s, 3H), 3.57 (s, 3H), 4.34-4.30 (m, 1H), 5.26-5.21 (m, 1H), 5.49 (dd, 1H), 6.72 (d, 1H), 7.11 (t, 2H), 7.62 (dd, 2H)

Procedure for Formation of Lactone (3R,5S) (b)

Tertiary-butyl (6-{(E)-2-[4-(4-fluorophenyl)-6-isopropyl-2-[methyl(methylsulfonyl)amino]pyrimidin-5-yl]ethenyl}(4R,6S)-2,2-dimethyl-1,3-dioxan-4-yl)acetate (20.0 g) was dissolved in acetonitrile (140 mL) at 40° C., then cooled to 35° C. before gradual addition of hydrochloric acid (0.02M, 35 mL) at 35° C. The resulting solution was stirred at 35° C. until the reaction was complete then cooled to 25° C. Acetonitrile (8 mL) and sodium hydroxide (1.0M, 38 mL) was added at 25° C. and the resulting mixture stirred at this temperature until the reaction was complete. Sodium chloride (18.8 g) was added and the mixture cooled to 0° C. Sodium chloride saturated hydrochloric acid (1 M) was then added to the stirred reaction mixture at 0° C. until a pH of 4 was achieved. The two phase system was allowed to settle at 0° C. and the lower aqueous phase was removed to waste. Toluene (250 mL) was added to the organic phase and mixture was distilled at atmospheric temperature until the mixture reached a temperature of 105° C. was achieved. The solution was then heated under azeotropic conditions for a further 6 hours at 105° C. The mixture was allowed to cool to ambient temperature before isolating the crystalline lactone. The material was washed with methyl t butyl ether (100 mL) before drying in a vacuum oven at 22° C. under nitrogen to yield 12.8 g of dry lactone.

$^1$H NMR (500 MHz, DMSO d6) δ: 1.23 (d+d, 6H), 1.64 (m, 1H), 1.76 (m, 1H), 2.40 (ddd, 1H),
2.66 (dd, 1H), 3.36 (spt, 1H)*, 3.46 (s, 3H), 3.56 (s, 3H), 4.08 (m, 1H), 5.16 (m, 1H), 5.26 (d, 1H), 5.57 (dd, 1H), 6.76 (dd, 1H), 7.31 (t, 2H), 7.70 (dd, 2H).
*Partially obscured Procedure for conversion of Lactone to Calcium Salt (1)

Aqueous sodium hydroxide (4% w/w, 38 ml) was added to a stirred solution of N-(4-(4-fluorophenyl)-5-{(E)-2-[{2S,4R}-4-hydroxy-6-oxotetrahydro-2H-pyran-2-yl]ethenyl}-6-isopropylpyrimidin-2-yl)-N-methylmethanesulfonamide (16 g) in acetonitrile (148 mL) at 20° C. The reaction held at 25° C. for 2.5 hour with stirring. Aqueous hydrochloric acid (29 mL, 0.1M) was added to adjust the pH of the solution to approximately pH10.5. Water (71 mL) was added so that the combined charge of water and hydrochloric acid (0.1 M) (from the previous pH adjustment step) was 100 mL. Toluene (125 ml) was then added and the mixture stirred at 40° C. for 30 minutes before it was allowed to settle for 1 hour at 40° C. The aqueous phase was then separated from the organic phase at 40° C. The aqueous phase was then distilled under reduced pressure (53 mBar, ≤40° C.) until the volume was reduced to 135 mL.

Water (35 mL) was added to bring the total volume to 170 mL. The solution was heated to 40° C. before addition of a solution of calcium chloride di-hydrate (3.05 g) in water (29.5 mL) over 20 min, maintaining the reaction mixture at 38-41° C.

The reaction mixture was stirred for a further 15 min at 40° C., then cooled to 20° C. and stirred at this temperature for a further 15 min. The resulting suspension was filtered, washed with water (3×53 mL) and dried to give (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt (17.13 g).

Synthesis of Starting Materials

Isopropyl-2-[(4R,6S)-6-formyl-2,2-dimethyl-1,3-dioxan-4-yl}acetate

Chlorine gas (2469.6 mL, 118 mmol) was charged to toluene (373.3 mL) at −60° C. Dimethyl sulphide (11.67 mL, 121 mmol) was then added dropwise to the cooled solution over 30 minutes, keeping the contents at −60° C. After 30 minutes at this temperature, isopropyl 2-[(4R,6S)-6-formyl-2,2-dimethyl-1,3-dioxan-4-yl]acetate (24.56 g, 95 mmol) in toluene (46.7 mL) was added dropwise to the vessel over 30 minutes, maintaining the internal temperature at −60° C. The reaction mixture was agitated at −60° C. for 30 minutes followed by the dropwise addition of triethylamine (26.36 g, 261 mmol) over 30 minutes, allowing the internal temperature to rise to −50° C. The reaction mixture was then allowed to warm to 25° C. evenly over 75 minutes. The resulting slurry was stirred at 25° C. for 30 minutes, then water (77 mL) was added and the mixture agitated for 30 minutes. The aqueous layer was separated and the pH checked (pH should be between 7.5 and 8.5). The resulting organic portion was washed with water (23.3 mL) and the organic portion separated for vacuum distillation at 150 mbar. Distillation was continued until ~350 mL of toluene had been removed. Toluene (350 mL) was added to the flask and the vacuum distillation repeated at 150 mbar to remove ~350 mL of toluene. The resulting solution was transferred to a flask containing activated 4 angstrom molecular sieves and left at ambient temperature overnight. This solution was used directly for the coupling stage.

Analogues with different ester groups R may be made as above with the following exceptions: for the methyl analogue, the distillations were performed at much higher vacuum (and therefore at lower temperatures).

Iso-propyl 2-[(4R,6S)-6-formyl-2,2-dimethyl-1,3-dioxan-4-yl}acetate

This compound may be made using the procedures described in EP0319847. Analogues with different ester groups R may be made by a similar method.

Diphenyl[4-(4-fluorophenyl)-6-isopropyl-2-[methyl(methylsulfonyl)amino]pyrimidin-5-ylmethyl]phosphine oxide This compound can be made as described in patent application WO00/49014

The invention claimed is:
1. A crystalline compound of formula (7),

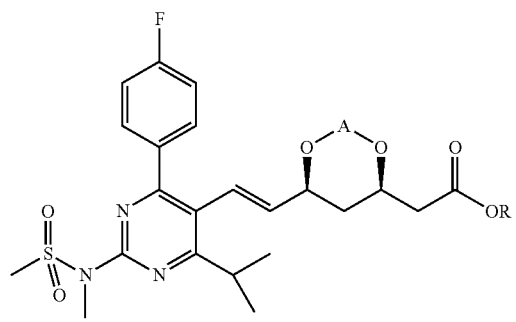

wherein
A is a ketal protecting group, and
R is (1-6C)alkyl,
which is methyl (E)-(6-{2-[4-(4-fluorophenyl)-6-isopropyl-2-[methyl(methylsulfonyl)amino]-pyrimidin-5-yl]vinyl}(4R,6S)-2,2-dimethyl[1,3]dioxan-4-yl)acetate having an X-ray powder diffraction pattern with peaks at 2-theta=9.5, 13.6 and 17.5.

2. A crystalline compound of formula (7),

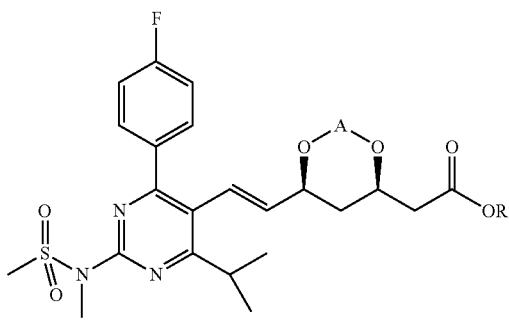

wherein
A is a ketal protecting group, and
R is (1-6C)alkyl,
which is ethyl (E)-(6-{2-[4-(4-fluorophenyl)-6-isopropyl-2-[methyl(methylsulfonyl)amino]-pyrimidin-5-yl]vinyl}(4R,6S)-2,2-dimethyl[1,3]dioxan-4-yl)acetate having an X-ray powder diffraction pattern with peaks at 2-theta=15.9, 18.4 and 19.5.

3. A crystalline compound of formula (7),

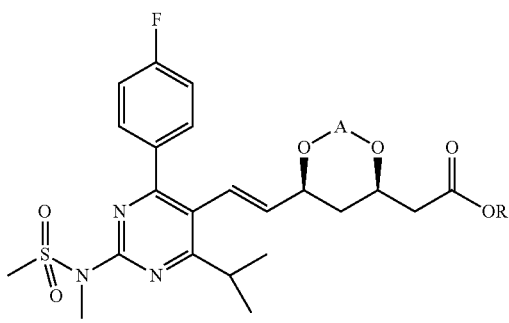

wherein
A is a ketal protecting group, and
R is (1-6C)alkyl,
which is iso-propyl (E)-(6-{2-[4-(4-fluorophenyl)-6-iso-propyl-2-[methyl(methylsulfonyl)amino]-pyrimidin-5-yl]vinyl}(4R,6S)-2,2-dimethyl[1,3]dioxan-4-yl)acetate having an X-ray powder diffraction pattern with peaks at 2-theta=7.8, 11.6 and 15.5.

4. A crystalline compound of formula (7),

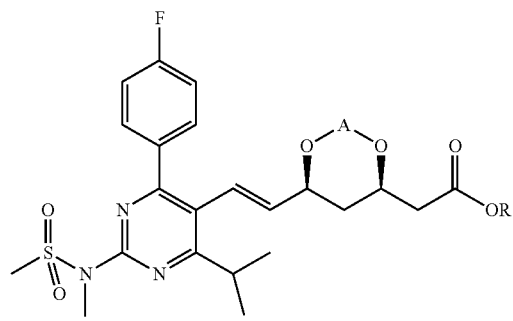

wherein
A is a ketal protecting group, and
R is (1-6C)alkyl,
which is n-hexyl (E)-(6-{2-[4-(4-fluorophenyl)-6-isopropyl-2-[methyl(methylsulfonyl)amino]-pyrimidin-5-yl]vinyl}(4R,6S)-2,2-dimethyl[1,3]dioxan-4-yl)acetate having an X-ray powder diffraction pattern with peaks at 2-theta=5.3, 7.1 and 18.9.

\* \* \* \* \*